United States Patent [19]
Comisarow et al.

[11] 3,937,955
[45] Feb. 10, 1976

[54] FOURIER TRANSFORM ION CYCLOTRON RESONANCE SPECTROSCOPY METHOD AND APPARATUS

[75] Inventors: Melvin Barnet Comisarow; Alan George Marshall, both of Vancouver, Canada

[73] Assignee: Nicolet Technology Corporation, Mountain View, Calif.

[22] Filed: Oct. 15, 1974

[21] Appl. No.: 514,505

[52] U.S. Cl. .............................. 250/283; 250/291
[51] Int. Cl.[2] ..................... H01J 39/34; B01J 59/44
[58] Field of Search ........... 250/281, 282, 283, 284, 250/290, 291; 324/.5 R

[56] References Cited
UNITED STATES PATENTS

| | | |
|---|---|---|
| 2,627,034 | 1/1953 | Washburn ........................ 250/291 |
| 3,461,381 | 8/1969 | Nelson ............................ 324/.5 R |
| 3,475,680 | 10/1969 | Anderson ........................ 324/.5 R |
| 3,505,517 | 4/1970 | Llewellyn ........................ 250/291 |
| 3,742,212 | 6/1973 | McIver ............................ 250/291 |

Primary Examiner—Craig E. Church
Attorney, Agent, or Firm—Christensen, O'Connor, Garrison & Havelka

[57] ABSTRACT

A gas sample is introduced into an ion cyclotron resonance cell enclosed in a vacuum chamber, and ionized. A magnetic field constrains ions to circular orbits. After an optional delay adequate to allow ion-molecule reactions to occur, a pulsed broad-band oscillating electric field disposed at right angles to the magnetic field is applied to the ions. As the frequency of the applied electric field reaches the resonant frequency of various ions, those ions absorb energy from the field and accelerate on spiral paths to larger radius orbits. The excited motion is sensed and digitized in the time domain. The result of the digitization is Fourier transformed into the frequency domain for analysis. If desired, a sequential series of pulsed broad-band oscillating fields can be applied and the resulting change in motion sensed, digitized and accumulated in a sequential manner prior to Fourier transformation.

43 Claims, 7 Drawing Figures

FOURIER TRANSFORM ION CYCLOTRON RESONANCE SPECTROSCOPY METHOD AND APPARATUS

BACKGROUND OF THE INVENTION

This invention relates to spectroscopy, and more particularly to ion cyclotron resonance spectroscopy.

Ion cyclotron resonance is well known, and provides a sensitive and versatile means for detecting gaseous ions. In this regard, it is well known that a moving gaseous ion in the presence of a static magnetic field is constrained to move in a circular orbit in a plane perpendicular to the direction of the magnetic field, and is unrestrained in its motion in directions parallel to the magnetic field. The frequency of this circular motion is directly dependent upon the strength of the magnetic field and the charge-to-mass ratio of the ion. When such orbiting ions are subjected to an oscillating electric field disposed at right angles to the magnetic field, those ions having a cyclotron orbital frequency equal to the frequency of the oscillating electric field absorb energy from the electric field and are accelerated to larger orbital radii and higher kinetic energy levels. Because only the resonant ions absorb energy from the electric field, they are distinguishable from non-resonant ions upon which the field has substantially no effect.

Various methods of and apparatus for taking advantage of the foregoing phenomena and utilizing it to measure the number of ions having a particular resonant frequency have been proposed and are in use. These devices are generally referred to as ion cyclotron resonance mass spectrometers.

In the omegatron type of ion cyclotron resonance mass spectrometer, gaseous ions are generated by bombardment of a gaseous sample with moving electrons. These ions are then subjected to mutually perpendicular magnetic and oscillating electric fields. The electric fields accelerate the resonant ions to higher velocities and larger oribtal radii. Ultimately these ions accelerate to a point where they impinge upon a collector plate. The resulting ion current is measured and recorded.

In another type of ion cyclotron mass spectrometer, ions having a resonant frequency equal to the frequency of the oscillating electric field are accelerated and the resultant power absorbed from the electric field is measured. The measured power is related only to the resonant ions, and not to ions having other resonant frequencies. Thus, detection of the absorbed power results in a measurement of the number of resonant gaseous ions of a particular mass-to-charge ratio present in a sample. Obviously, an ion mass-to-charge ratio spectrum of a particular ionized gas sample is obtained by scanning and detecting. Scanning can be accomplished by varying the frequency of the oscillating electric field, the strength of the applied magnetic field, or both, so as to bring ions of differing mass-to-charge ratios into resonance with the oscillating electric field. An example of an ion cyclotron resonance mass spectrometer utilizing such a power absorption detection technique is described in U.S. Pat. No. 3,390,265 entitled "Ion Cyclotron Resonance Mass Spectrometer Means for Detecting the Energy Absorbed by Resonance Ions" issued to Peter M. Llewellyn on June 25, 1968.

Other U.S. patents disclosing various related ion cyclotron resonance mass spectrometers methods and apparatus, and improvement thereto, are: U.S. Pat. No. 3,446,957 entitled "Ion Cyclotron Resonance Spectrometer Employing Means for Recording Ionization Potentials" issued to David E. Gielow et al on May 27, 1969; U.S. Pat. No. 3,475,605 entitled "Ion Cyclotron Double Resonance Spectrometer Employing a Series Connection of the Irradiating and Observing RF Sources to the Cell" issued to Peter M. Llewellyn on Oct. 28, 1969; U.S. Pat. No. 3,502,867 entitled "Method and Apparatus for Measuring Ion Interrelationships by Double Resonance Mass Spectroscopy" issued to J. L. Beauchamp on Mar. 24, 1970; U.S. Pat. No. 3,505,516 entitled "Ion Cyclotron Resonance Spectrometer Employing an Optically Transparent Ion Collecting Electrode" by D. E. Gielow et al issued Apr. 7, 1970; U.S. Pat. No. 3,505,517 entitled "Ion Cyclotron Resonance Mass Spectrometer with Means for Irradiating the Sample with Optical Radiation" issued to P. M. Llewellyn on Apr. 7, 1970; U.S. Pat. No. 3,511,986 entitled "Ion Cyclotron Double Resonance Spectrometer Employing Resonance in the Ion Source and Analyzer" issued to P. M. Llewellyn on May 12, 1970; U.S. Pat. No. 3,535,512 entitled "Double Resonance Ion Cyclotron Mass Spectrometer for Studying Ion-Molecule Reactions" issued to J. D. Baldeschwieler on Oct. 20, 1970; and U.S. Pat. No. 3,677,642 entitled "Ion Cyclotron Resonance Stimulated Low-Discharge Method and Apparatus for Spectral Analysis" issued to J. D. Baldeschwieler on July 18, 1972.

In general, all of the foregoing patents disclose ion cyclotron resonance mass spectrometers wherein adverse space charge effects are reduced by continuously ionizing a gas sample within a first region of a sample chamber, and subjecting the ions thus produced to transverse magnetic and static electric fields. These fields move the ions along cycloidal paths in a direction perpendicular to both fields to a second region of the same sample chamber removed in space from the first region. In the second region, the ions are subjected to the combined influence of the magnetic field and an oscillating electric field lying at right angles thereto. In accordance with general ion cyclotron resonance phenomena discussed above, the ions having a resonant frequency equal to the frequency of the oscillating electric field absorb energy from that field and the energy absorption is detected to provide a measure of the number of such resonant ions. Because the resonant ions are detected in a second analyzing region, which is spatially distinct from the first ionizing region, the effect of space charge in the analysis is reduced.

A U.S. patent disclosing a somewhat different type of ion cyclotron resonance mass spectrometer is U.S. Pat. No. 3,742,212 entitled "Method and Apparatus for Pulsed Ion Cyclotron Resonance Spectroscopy" issued to Robert T. McIver, Jr. on June 26, 1973. The spectrometer disclosed in this patent includes a single-section ion cyclotron resonance cell. In this cell, ions are formed during a known first time period, allowed to react with neutral molecules for a second time period, and detected in a third time period. The detection of ions of a particular mass-to-charge ratio is achieved by suddenly changing the resonant frequency of the desired mass-to-charge ratio ions so as to equate their resonant frequency to the fixed frequency of a marginal oscillator detector. (Except during the "detect" time period, the ion cyclotron frequencies are not equal to the marginal oscillator frequency.) The marginal oscillator frequency then provides an output signal proportional to the number of ions that absorb energy from it at a given instant of time. The required sudden change in the cyclotron frequency of the ions of a given mass-to-charge ratio is achieved either by a sudden change in the value of the applied magnetic field or by a sudden change in the magnitude of the static electric field which is used to "trap" the ions in the ion cyclotron resonance cell. An alternative means for initiating the ion cyclotron resonance detection period is to suddenly change the amplitude of the radio frequency level of the marginal oscillator from zero volts to some higher level. After the ion cyclotron resonance detection period is completed, a "quench" electric field pulse is applied to remove all ions from the ion cyclotron resonance cell. The total operational sequence (ion formation, delay period for ionmolecular reactions, ion cyclotron resonance detection, ion removal) is then repeated.

One of the major disadvantages of all of the above-noted prior art ion cyclotron mass resonance spectroscopy methods and apparatus is that ion cyclotron resonance detection is limited to a single frequency (and therefore a single mass-to-charge ratio) at any instant in time. In order to obtain a wide-range mass-to-charge ratio spectrum of a given ionized gaseous sample, it is necessary to vary either the magnetic field (or the frequency of the oscillating electric field, or both) so as to equate the resonance of the various ions with the resonance of the oscillating electric field. In this regard, by way of example, using a fixed oscillator detector frequency of 153 KHz, it requires about 25 minutes to obtain a typical mass-to-charge ratio spectrum by varying the applied magnetic field by an amount adequate to cover a mass range of 15 atomic mass units to 240 atomic mass units, for singly charged ions.

Therefore, it is an object of this invention to provide a new and improved method of and apparatus for ion cyclotron resonance spectroscopy that provides a wide-range mass-to-charge ratio spectrum for a given ionized sample in a relatively short period of time.

In addition to the slow spectrum processing time of prior art ion cyclotron methods and apparatus, other disadvantages exist. For example, the resolution of the resultant signals is relatively fixed and cannot easily be varied to improve the accuracy of the resultant information. More specifically, prior art methods and apparatus are not readily adapted to vary the resultant signal-to-noise ratio in order to improve resolution. It will be appreciated that the ability to trade one of these factors against the other is of particular importance when the sample being analyzed is very dilute.

Therefore, it is also an object of this invention to provide a new and improved method of and apparatus for ion cyclotron spectroscopy wherein resolution and signal-to-noise ratio can be readily varied.

The utilization of Fourier transform techniques in infra-red and nuclear magnetic resonance spectroscopies has been proposed by the prior art. In general, Fourier transform techniques provide for the detection of a complete speectrum of information in the time normally required to scan through a single frequency-resolution element using conventional scanning techniques. In this regard, U.S. Pat. No. 3,475,680 entitled "Impulse Resonance Spectrometer Including a Time Averaging Computer and Fourier Analyzer" issued to W. A. Anderson et al on Oct. 28, 1969 suggests the use of Fourier techniques in a variety of spectroscopies; however, not ion cyclotron resonance spectroscopy. Further, U.S. Pat. No. 3,530,371 entitled "Internal Field-Frequency Control for Impulse Gyromagnetic Resonance Spectrometers" issued to F. A. Nelson et al on Sept. 22, 1970, suggests a Fourier method for the specialized purpose of controlling the magnetic field intensity in various spectrometers, including ion cyclotron resonance spectrometers. Finally, U.S. Pat. No. 3,461,381 entitled "Phase Sensitive Analog Fourier Analyzer Read-Out for Stored Impulse Resonance Spectral Data" issued to F. A. Nelson et al on Aug. 12, 1969 suggests an analog techique for obtaining the Fourier transform of a nuclear magnetic free-induction response to a pulse magnetic field excitation. This technique is suggested for application to ion cyclotron resonance spectrometers. While this and other similar prior art does broadly suggest the application of Fourier techniques to ion cyclotron spectroscopy, they do not disclose a method of or apparatus for utilizing Fourier transform techniques to provide a Fourier transform ion cyclotron resonance spectrometer. In fact, these patents merely disclose impulse excitation of the transient spectral response, which excitation is not particularly suitable for utilization in a Fourier transform ion cyclotron resonance spectrometer for reasons which are set forth below.

Therefore, it is a general object of this invention to provide a new and improved method of and apparatus for ion cyclotron resonance spectroscopy.

It is a further object of this invention to provide a Fourier transform ion cyclotron resonance spectrometer.

It is yet another object of this invention to provide a method of ion cyclotron resonance spectroscopy that utilizes Fourier transform techniques to obtain a spectrum of ion cyclotron resonance information.

It is yet another object of this invention to provide a Fourier transform ion cyclotron resonance spectrometer suitable for obtaining an ion cyclotron resonance spectrum of a specified mass-to-charge range and resolution in a time period much shorter than that required by prior art ion cyclotron resonance spectrometers.

It is a subsidiary object of this invention to provide an ion cyclotron resonance spectrometer that employs a fixed-field magnet for generating the necessary magnetic field.

It is yet another object of this invention to provide an apparatus for exciting ions of many different mass-to-charge ratios in a short period time and rapidly detecting the excited ion cyclotron motion of such ions.

It is a further object of this invention to provide a method of and an apparatus for ion cyclotron resonance spectroscopy that provides a technique for reducing the effect of erroneous information created by noise and the like.

SUMMARY OF THE INVENTION

In accordance with a preferred form of this invention a gas sample is admitted into an evacuable chamber within which a trapped ion analyzer cell is disposed. In its preferred form, the cell includes four electrode side plates, which may be curved, and a pair of electrode end (trapping) plates. The gas sample is ionized within this cell by a suitable ionizing source, such as an electron beam pulsed through the cell. These ions are trapped within the cell by the application of a low DC trapping potential of one polarity to the trapping plates and a smaller magnitude DC potential to the other plates. The ions within the cell are subjected to a unidirectional magnetic field that causes them to move in circular orbits in the plane perpendicular to the magnetic field direction. Following ion formation, and double irradiation, if desired, and a known delay period in which ionmolecular reactions may proceed, if desired, the ions in the cell are excited by a pulsed broad-band oscillating electrical field applied in a direction perpendicular to the applied magnetic field. The excited ion cyclotron motion of all of the excited ions is sensed by a broad-band amplifier, digitized by a high-speed analog-to-digital converter, and, preferably, the digitized transient response is added point-by-point to the existing sum of previous digitized signals from preceding cycles of operation. All ions are then removed from the ion cyclotron resonance cell by a "quench" electric field pulse created by applying a pulsed DC potential to one or more of the plates of the trapped ion analyzer cell. Thereafter, the cycle of operation is repeated.

After the digitized transient ion cyclotron resonance information generated by a predetermined number of cycles of operation is accumulated, it is Fourier transformed to produce a frequency-domain ion cyclotron resonance spectrum. By suitable phase adjustments made at the time of Fourier transformation, it is possible to extract a spectral display comprising dispersion, absorption or absolute-value information. By varying the time delay period between ion formation and ion excitation and detection, the sample concentrations of ions of any mass-to-charge ratio lying within a specified mass-to-charge ratio range may be obtained as a function of time following ion formation. Further, ion cyclotron double resonance spectroscopy may be readily carried out by irradiating ions of one or more selected mass-to-charge ratios with a pulsed oscillating electric field that excites resonances at the appropriate mass-to-charge ratio(s) prior to the application of the usual excitation pulse.

It will be appreciated at this point that the invention provides a Fourier transform ion cyclotron resonance spectroscopy method and apparatus. The invention overcomes many of the disadvantages of prior art devices. Specifically, the invention provides an entire spectrum of information in essentially the same time the prior art requires to obtain information related to a particular resonant frequency. Further, because a broad-band spectrum of information is rapidly obtainable utilizing the method and apparatus of the invention, double resonance spectroscopy information is obtained in a more rapid and accurate manner. In addition, very dilute samples can be analyzed using the present invention because information accumulation is very rapid and, in addition, can proceed in a manner such that resolution can be traded off against signal-to-noise ratio. For example, better resolution can be obtained if the information acquisition period is made longer. On the other hand the signal-to-noise ratio will be improved to the detriment of resolution if the acquisition period is made shorter, using the same total observation period.

BRIEF DESCRIPTION OF THE DRAWINGS

The foregoing objects and many of the attendant advantages of this invention will become more readily appreciated as the same becomes better understood from the following more detailed description of a preferred embodiment of the invention when taken in conjunction with the accompanying drawings wherein.

DESCRIPTION OF THE PREFERRED EMBODIMENTS

Figure 1:
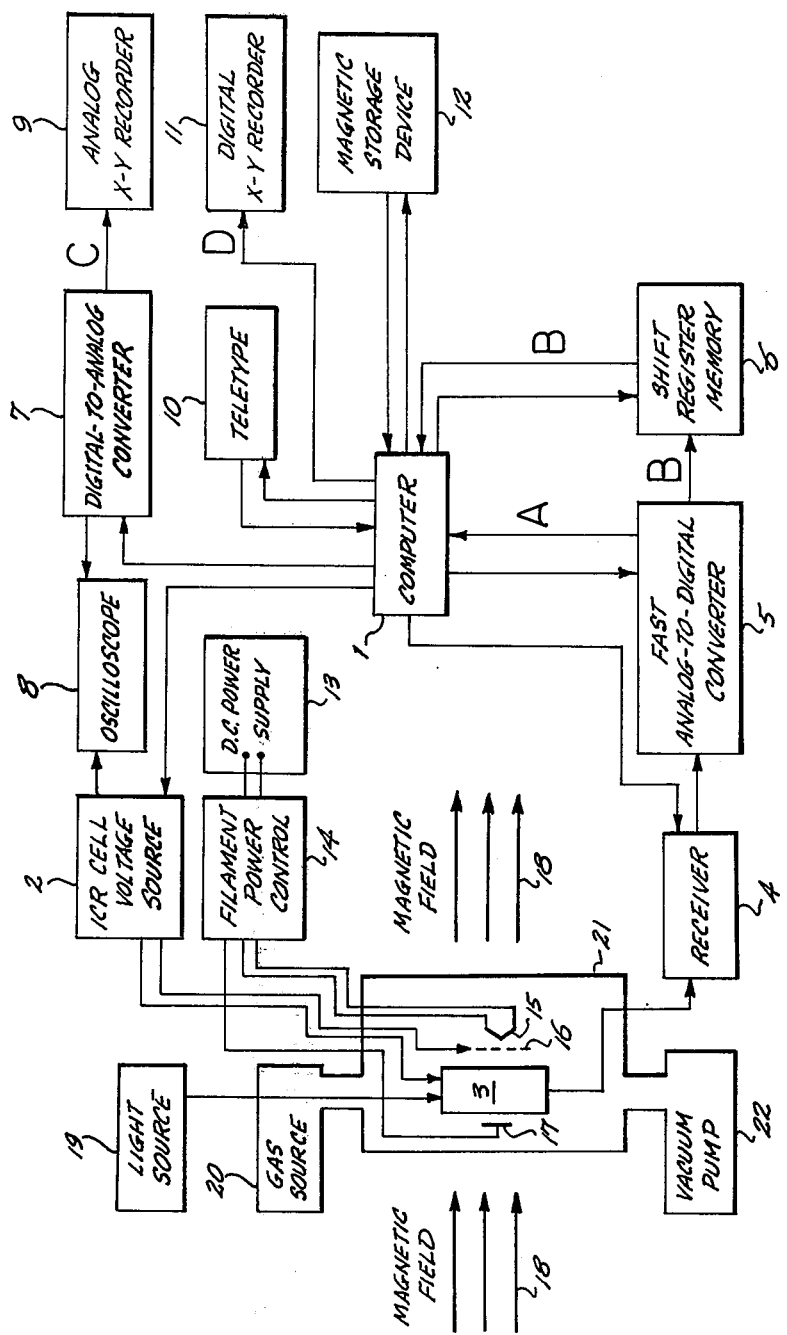
FIG. 1 is a block diagram of a preferred embodiment of the invention.

FIG. 1 illustrates an ion cyclotron resonance cell 3 enclosed in an evacuable chamber 21. The chamber 21 is evacuated to a suitably low pressure (say $10^{-8}$ torr) by a suitable vacuum pump 22. The vacuum pump 22 may consist of any one of many well known pumps which are capable of achieving a low pressure in the desired range, such as a sputter-ion pump, a sublimation pump, a diffusion pump with the necessary traps, or the like. Initial evacuation of the chamber 21 is achieved with a mechanical forepump, or a refrigerated sorption pump, if desired. Further, the evacuable chamber 21 and the vacuum pump 22 may be heated with a heating jacket (not shown) to aid in evacuation, if desired.

Once pump-down to $10^{-8}$ or so torr is attained, the gaseous sample to be analyzed is introduced into the evacuable chamber from a suitable gas source 20. Gas is supplied until a pressure in the range of $10^{-4}$ to $10^{-7}$ torr is achieved. Thereafter, dynamic pressure balance is maintained by continuous pumping and leaking of gas into the evacuable envelope. Alternatively, following pump-down and subsequent isolation of the pump 22 from evacuable envelope 21 by a valve (not shown), a gas sample may be introduced from a gas source 20 until a static pressure in the range of $10^{-4}$ to $10^{-7}$ torr is achieved.

Figure 2:
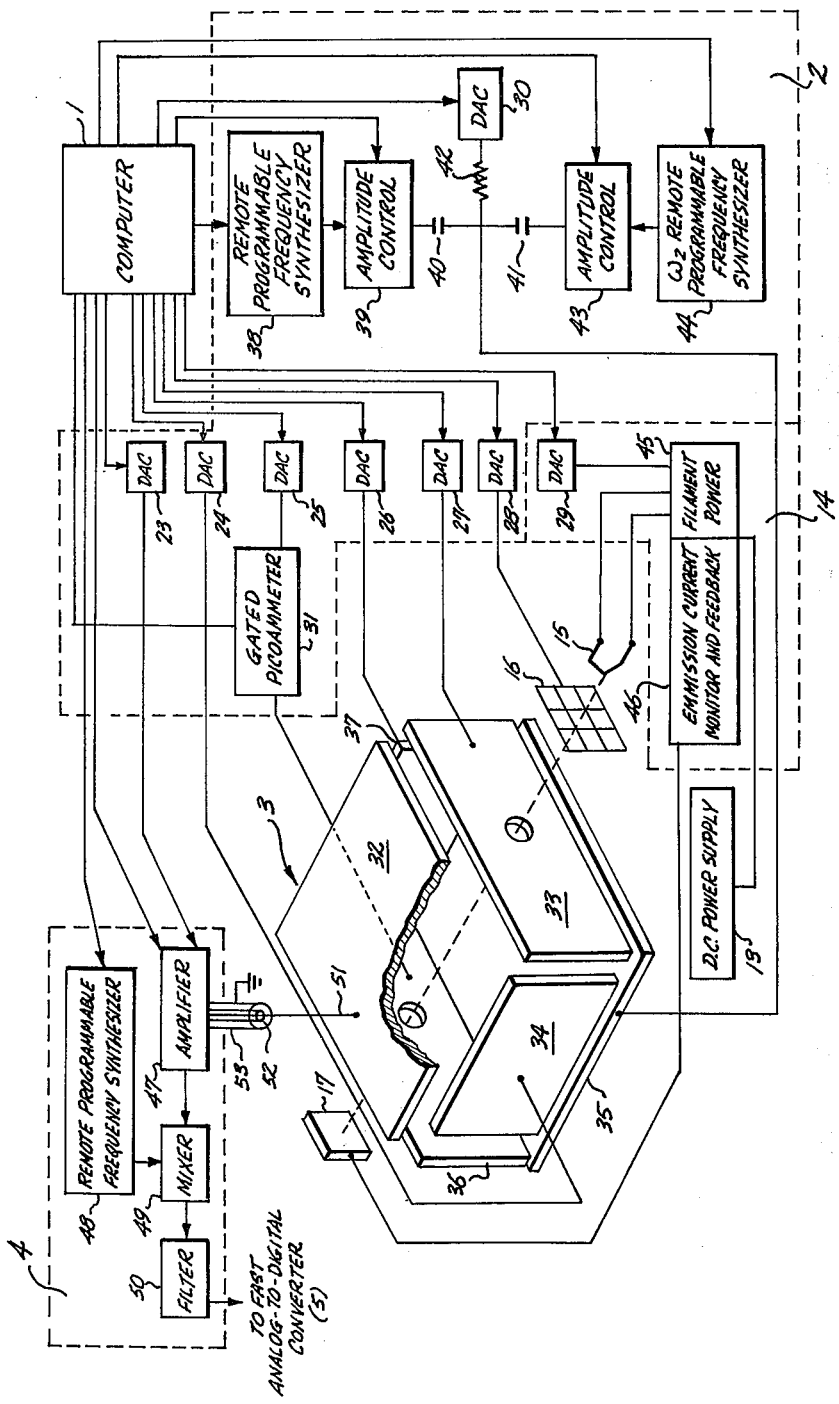
FIG. 2 is a partially pictorial and partially block diagram, in somewhat more detail, of a preferred embodiment of the invention.
Figure 4:
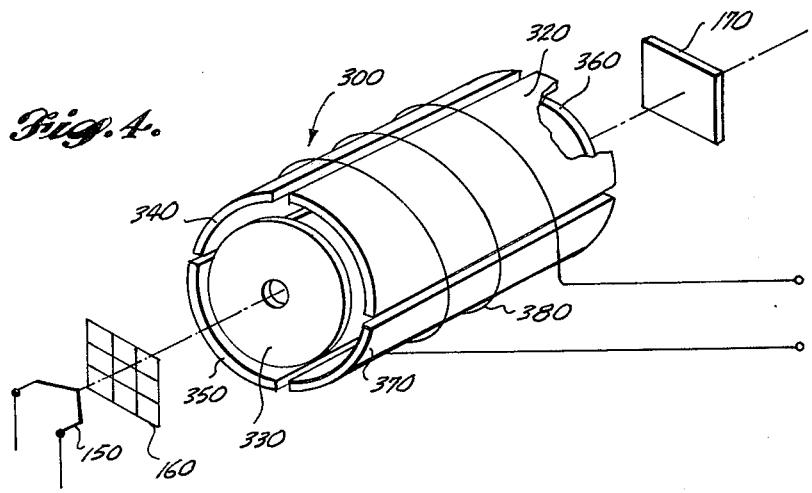
FIG. 4 is a pictorial diagram of an alternative embodiment of a trapped ion cell formed in accordance with the invention and suitable for use in the embodiment of the invention illustrated in FIGS. 1 and 2.

The ion cyclotron resonance cell may take on various forms. FIG. 2 illustrates a parallelepiped form and FIG. 4 illustrates a generally cylindrical form, and is discussed below. In either case, the cell includes six electrodes or plates. The plates define the sides and ends of the parallelepiped form. The parallelepiped cell, thus, includes a first pair of side plates 34 and 37, a second pair of side plates 32 and 35, and a pair of end or trapping plates 33 and 36. The plates are formed of any suitably conductive material such as molybdenum or rhodium-plated beryllium copper, stainless steel, or the like, and are held in fixed positions within the evacuated chamber 21 by any suitable insulating supporting means, not shown.

An ionizing beam source such as an electron gun comprising a filament 15 and a control grid 16 is mounted within the chamber 21 so as to discharge a stream of electrons through suitable apertures in the trapping plates toward a collector electrode 17. The orientation of the ion cyclotron resonance cell and, thus, the ionizing beam source inside of the evacuable chamber is such that the electrons are discharged in a direction parallel to a fixed, externally applied magnetic field 18. In the case of the cylindrical ion cyclotron resonance cell, the magnetic field may be created by a toroidal winding wrapped around the side plate and having a longitudinal axis that coincides with the longitudinal axis defined by the electron beam, as discussed below with respect to FIG. 4.

In operation, the bias voltage applied to the control grid 16 is pulsed in the manner hereinafter described to allow a burst of electrons generated by the filament to pass therethrough. The thusly generated electron beam then passes through the aligned apertures in the trapping plates 33 and 36 and are collected at the collector electrode 17. Ionization of the gas sample is effected by collision of the electrons with the gas, with all primary ions being formed within the cell during passage of the burst of electrons therethrough.

By way of illustration, the voltage on the filament 15 is maintained at any suitable level, such as −15 volts by a filament bias digital-to-analog converter 29 forming a portion of a filament power control 14. The filament power control 14 also includes an emission current monitor and feedback circuit 46 connected to the collector electrode 17 and a filament power source 45 biased by the filament bias digital-to-analog converter 29. In this regard, the control grid 16 is normally maintained at a suitable voltage level such as −20 volts. This voltage is controlled by a grid digital-to-analog converter 28 forming part of an ICR cell voltage source 2. The ICR voltage source 2 is, in turn, under the control of a computer 1.

When at its normal voltage level (e.g. −20 volts), the grid digital-to-analog converter 28 cuts off the flow of electrons through the cell 3. Periodically, every 100 milliseconds, for example, a voltage pulse of a different level, such as −10 volts, for example, is applied to the control grid by the grid digital-to-analog converter 28 for a suitable time period (e.g. 1 microsecond to 10 milliseconds). This change in voltage level permits the ionizing beam to pass through the grid and, thus, through the cell for this "ionizing" time period. The collector plate is maintained at any suitable voltage level (such as between +10 and +20 volts) by the emission current monitor and feedback circuit 46. Thus, in a conventional manner the collector plate 17 recaptures secondary electrons emitted upon primary electron impact.

The emission current monitor and feedback circuit 46 also senses the electron current generated at the collector plate and provides a feedback signal to the filament power supply 45. In accordance with this signal, the filament power supply 45 applies power to the filament 15 adequate to keep emission current constant during the ion formation time period. Alternatively, if desired, ion formation during a controlled time period may also be achieved by changing the filament bias voltage to a negative value from a normal positive value and thereby control the electron beam flow through the ion resonance cell 3. Obviously, other means for ionizing the gas molecules may also be employed, including the use of ionizing beams of particles other than electrons and electromagnetic radiation. Furthermore, it is not absolutely necessary that ionization be conducted only along a line parallel to the magnetic field direction 18. If desired, for example, ionization may be effected by a light source 19 (FIG. 1) along a line orthogonal to the second pair of side plates 34 and 37.

As will be understood by those skilled in the art, the ions formed by electron impact and trapped within the ion resonance cell 3 by the various voltages applied to the plates, as herein described, are constrained by the unidirectional magnetic field 18 to circular orbits in a plane normal to the direction of the magnetic field. The angular cyclotron frequency, $\omega_c$, of this motion (in mks units) is:

$$\omega_c = (q/m)B \quad (1)$$

where:
(q/m) = charge-to-mass ratio of the ion; and,
B = the magnetic field strength.

The ions are trapped within the cell by voltages applied to the various plates. The voltages are generated by the ICR cell voltage source 2 which includes a plurality of digital-to-analog converters controlled by the computer 1. For normal operation of the spectrometer with positive ions, static voltages are applied to trapping plates 33 and 36 by trapping plate digital-to-analog converters 25 and 27. These trapping plate static voltages are normally equal to about +1 volt with respect to the static voltages applied to the other plates of the cell. For reasons hereinafter discussed, a gated picoammeter 31 is connected between the output of the digital-to-analog converter 25 connected to the trapping plate nearest the collector 17, and that trapping plate.

The static voltages applied to the four other plates 32, 34, 35 and 37 are generated by four other digital-to-analog converters 23, 24, 30 and 26 respectively. If negative ions are to be analyzed utilizing the method and apparatus of the invention, then the voltages applied to the trapping plates 33 and 36, will be negative with respect to the voltages applied to the other plates of the ion resonant cell. In any event, the required digital control signals for the various digital-to-analog converters are all provided by the computer 1, as illustrated in FIG. 2. The computer, in turn, is under the control of any suitable communication source, such as the teletype 10 illustrated in FIG. 1.

Figure 3:
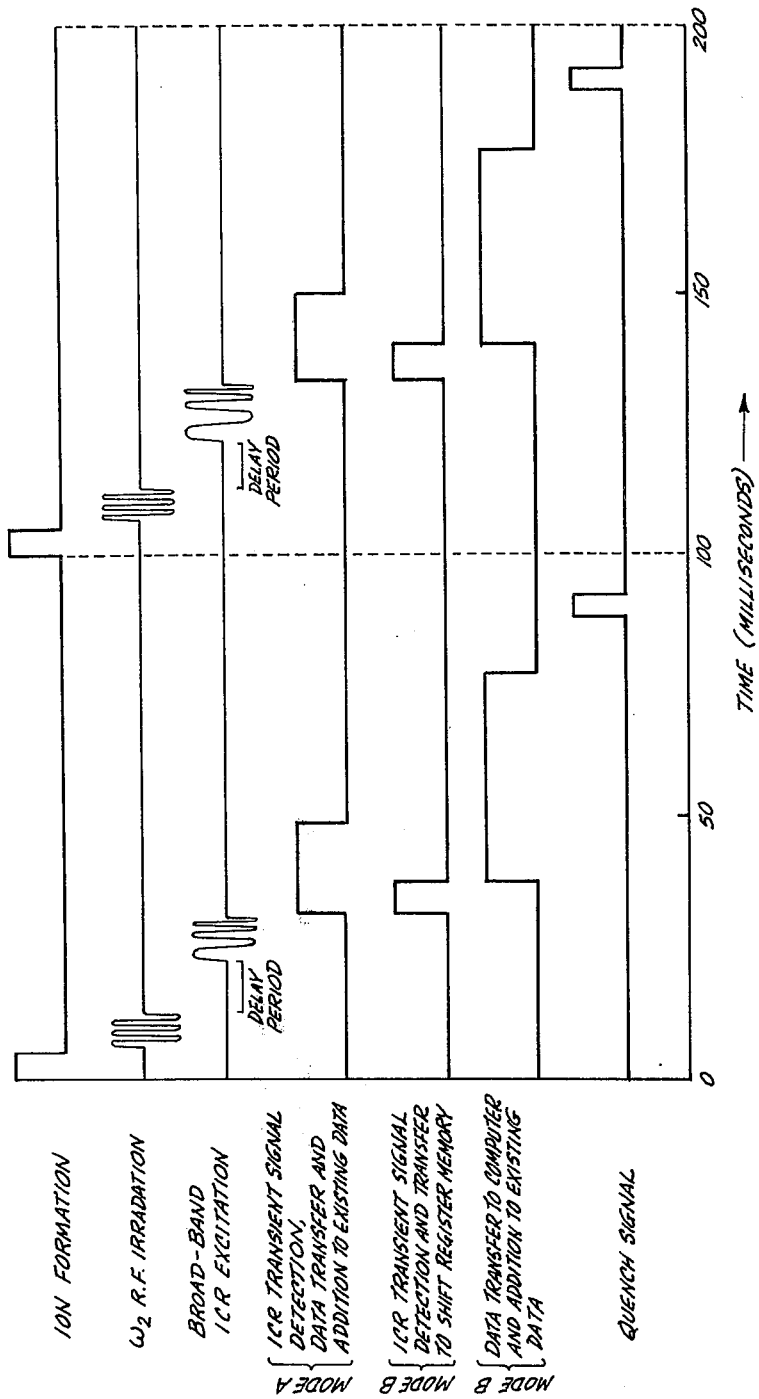
FIG. 3 is a timing diagram illustrating the sequence of signal application and signal formation in the preferred embodiment of the invention herein described.

As illustrated in FIG. 3, the ion formation pulse, generated by the electron gun, is only the first step in the sequence of steps of the present invention. Following ion formation, the kinetic energy of ions of any selected mass may be increased by the application of a pulsed radio frequency (RF) electric field transverse to the direction of the magnetic field 18. Obviously the frequency, $\omega_2$, of this field is made equal to the resonance frequency of the selected ions, according to equation (1).

FIG. 2 illustrates two alternate apparatus of producing the required pulsed RF electric field. First, the required radio frequency electric field may be produced by a controllable remote programmable frequency synthesizer 38 controlled by the computer 1. As will be better understood from the following discussion this same frequency synthesizer is utilized to create the pulsed broad-band oscillating electric field hereinafter described. If the pulsed RF electric field is generated in this manner, it is applied through an amplitude control circuit 39 and a first coupling compacitor 40 to one of the side plates 35 (or 350).

The alternative method of creating the required pulsed RF electric field is to utilize an entirely separate programmable frequency synthesizer, designated $\omega_2$ remote programmable frequency synthesizer 44 in FIG. 2. The $\omega_2$ remote programmable frequency synthesizer 44 is also under the control of the computer 1. The output of the $\omega_2$ remote programmable frequency synthesizer 44 is applied through a separate path including a second amplitude control 43 and a second coupling capacitor 41 to the side plate 35 (or 350). For radio frequency blocking, a blocking resistor 42 is connected between the side plate 35 which receives the pulsed RF electric field and its associated digital-to-analog converter 30. The amplitude control circuits 39 or 43 control both the amplitude and pulse duration time of the output of their associated frequency synthesizers 38 and 44, in accordance with control signals generated by the computer 1.

FIG. 3 also illustrates that, following the application of pulsed RF electric field ($\omega_2$), the ions trapped in the ion resonance cell 3 are allowed to react with neutral molecules for a specified delay period, if desired, before ion cyclotron resonance detection is initiated.

The invention excites the trapped ions by applying a pulsed broad-band radio frequency electric field across the ion resonance cell 3, as illustrated on line 3 of FIG. 3. The field is applied in a direction transverse to the direction of the applied magnetic field 18. FIG. 2 illustrates the preferred apparatus for creating the required pulsed broad-band radio frequency electric field. Specifically, the computer 1 controls the controllable remote programmable frequency synthesizer 38 in a manner such that it generates a pulsed broad-band radio frequency electric field. The output of the remote programmable frequency synthesizer 38 is amplitude controlled by its associated amplitude control 39. The output of the amplitude control 39 is coupled via the coupling capacitor 40 to plate 35 of the cell 3. The radio frequency blocking resistor 42 prevents the output of the remote programmable frequency synthesizer 38 from affecting the operation of the digital-to-analog converter 30 associated with the plate 35 receiving the broad-band radio frequency electric field.

As discussed above, the amplitude control 39 is controlled by the computer 1. The control of the synthesizer 38 is such that during the time interval that the amplitude control 39 is gated on, the computer 1 provides a sequential frequency-programming input to the remote programmable frequency synthesizer 38. The input to the frequency synthesizer is such that it generates a broad-band radio frequency electric field that covers the cyclotron frequencies of all ions in a given mass-to-charge range (or ranges) in the ion resonance cell 3. Thus, all ions falling within a desired range are irradiated at their resonant ion cyclotron frequencies during the irradiation period. The simplest (but by no means the only) manner in which this result may be achieved is to control the remote programmable frequency synthesizer in a manner such that it produces a radio frequency signal which varies linearly from a low frequency value to a high frequency value during the period of time the associated amplitude control 39 is gated on, as shown schematically in FIG. 3.

If desired, other apparatus for exciting the ion cyclotron resonance of ions of a wide range of mass-to-charge ratios may also be utilized by the invention. All that is required is that the ion cyclotron motion of all specified ions be excited during the excitation period, i.e., the period during which the amplitude control 39 is gated on by the computer 1. For example, the remote programmable frequency synthesizer 38 may be frequency swept from a high value to a low value. Or, the output may be frequency swept back and forth between high and low values. Further, the frequency variation may be nonlinear with respect to time. Alternatively, the remote programmable frequency synthesizer 38 may be replaced by a suitable pseudo-random digital voltage sequence whose frequency components span the frequency range of interest. In this regard, as will be appreciated by those skilled in the art, suitable pseudo-random sequences can be readily extracted from the binary sequences generated by shift registers (shift register "codes").

A further alternative apparatus for creating a suitable electric field across the ion cyclotron resonance cell is formed by merely replacing the remote programmable frequency synthesizer 38 with a pulse amplifier. In this regard, since it is well known that the Fourier transform of a sine-wave pulse of duration $\tau$ seconds is a frequency function which is essentially flat over the frequency range $\pm \frac{1}{4} \tau$ Hz centered at the frequency of the sine wave of the original pulse, it is possible to achieve an essentially uniform irradiation field over a frequency range from about d-c to about 2M Hz by the application of a d-c pulse of about 100 nsec duration. However, the amplitude of such a pulse must be very large if the pulse is to be adequate to create excitation over that entire frequency range. In general, ion cyclotron resonance excitation over any arbitrary frequency bandwidth can be achieved by the generation of a pulse of a suitable duration, i.e., an excitation electric field having a frequency bandwidth of $\frac{1}{4} \tau$ Hz, centered at the pulse frequency, will result when a pulse of duration $\tau$ is generated and applied to one of the plates of the ion resonance cell.

The excitation of the ion cyclotron resonance of ions of many different mass-to-charge ratios over a short period of time, 3 milliseconds, for example, is one of the principal advantages of the present invention over the prior art. Because the ions whose motion has been excited by an excitation pulse of the type described above will orbit at their respective cyclotron frequencies [given by equation (1)], they will introduce an alternating voltage at their respective cyclotron frequencies in the plates of the ion cyclotron resonance cell. Any of these plates may be used to sense these frequencies, plate 32 being utilized in the illustrated embodiment of the invention. The simultaneous detection of the voltages induced by all of the excited ions in the ion cyclotron resonance cell 3 is the second principal advantage of the present invention.

Detection of the ion cyclotron resonance signals is accomplished by means of a receiver 4. The receiver, preferably, includes a high-gain broad-band amplifier 47, a mixer 49, a remote programmable frequency synthesizer 48 and a filter 50. The output of the broad-band amplifier 47, which receives the signal from the detecting plate 32, is applied to one input of the mixer 49. The remote programmable frequency synthesizer 48, forming a portion of the receiver 4, is controlled by the computer 1 and its output is applied to the second input of the mixer 49. The output of the mixer 49 is connected to the input of the filter 50. The output of the filter 50, which is the output of the receiver 4, is applied, as illustrated in FIG. 1, to a fast analog-to-digital converter 5.

The receiver 4 operates in the following manner: following the termination of the excitation pulse, the ion cyclotron resonance response signal is sensed by the high-gain broad-band amplifier 47, which may be a gated amplifier and, if so, is gated on by a suitable signal from the computer 1. The ion cyclotron resonance response signal detected by the broad-band amplifier 47 consists of a plurality of distinct signal frequencies, each frequency being related to excited ions of a distinct mass-to-charge ratio, with individual frequency component amplitudes being proportional to the respective number of ions having a particular mass-to-charge ratio. In other words, frequency is related to the mass-to-charge ratio and amplitude is related to the number of ions of a distinct mass-to-charge ratio. This signal is amplified by the broad-band amplifier 47 and mixed by the mixer 49 with the output of the remote programmable frequency synthesizer 48. The remote programmable frequency synthesizer 48 acts as a local oscillator. The difference frequency output of the mixer is filtered by the low-pass filter 50 and applied to the fast analog-to-digital converter 5.

The purpose of the mixer/synthesizer/filter assembly is simply to extract only a portion of the total amplified frequency spectrum, and shift it in frequency. By way of example, for a magnetic field of one tesla and a mass range of one to two hundred atomic mass units, ion cyclotron resonance frequencies for singly charged ions lie in the range between 15.3 MHz and 76.5 kHz. If it is desired to extract the ion cyclotron resonance spectrum only for masses lying in the range between 30 atomic mass units (510 kHz) and 50 atomic mass units (306 kHz), the remote programmable frequency synthesizer 48 might, for example, be programmed to generate a 300 kHz signal and the filter 50 adjusted to pass all frequencies below 230 kHz. The result of this adjustment of the apparatus of the invention is the extraction of the 0–230 kHz band of frequencies from 300 kHz to 530 kHz from the ion cyclotron resonance spectrum and shifting of each frequency downward by 300 kHz. This frequency shifting process is particularly useful when it is desired to achieve high mass resolution, as described below. In some situations, it may not be desirable to shift the output in frequency. For example, a shift is not desirable when the widest possible mass-to-charge ratio is to be observed. If such is the case, the output of the amplifier 47 should be directly connected to the input of the filter 50.

Preferably the amplifier 47 includes a preamplifier and a remotely located post-amplifier. In addition, it may also include a means for applying a positive feedback signal to the coaxial shield 52 surrounding the lead 51 running to the sensing plate 32 in order to minimize the capacitive loading seen by the sensing plate 32. Preferably, the coaxial shield 52 is in turn surrounded by an outer coaxial shield 53 which is connected to electrical ground. Preferably, the triaxial assembly consisting of the lead, and the two shields, extends through a wall of the evacuable chamber 21. The filter 50 may be either of the active or passive type and, preferably, is tunable. Since the requisite technology for creating amplifiers, filters and mixers of the type described above is well known, no further discussion is deemed necessary here.

The output of the receiver 4 is converted from analog form to digital form by the fast analog-to-digital converter 5 upon the occurrence of a suitable command signal generated by the computer 1. The required digitizing rate of the analog-to-digital converter 5 is $2f_{max}$ where $f_{max}$ if the highest frequency signal (in Hz) passing through the filter 50. Generally 8 or 9 bit accuracy in digitation of a given analog signal is adequate. Since the actual digitizing rate required for a given experiment is determined by the lowest mass-to-charge ratio of ions in the mass range of interest and by the number of atomic mass units in that mass range, the rate of digitization is variable and controlled by the computer 1. Since the technology for digitizing analog signals falling within the typical ion cyclotron resonance frequency range of 10 kHz to 5 MHz is well known, it will not be further discussed here.

FIG. 1 illustrates two different paths for the output of the fast analog-to-digital converter. The first path is designated A and extends to the computer 1 and the second path is designated B and extends to the computer 1 through a shift register memory 6. These paths are illustrated in time form in FIG. 3. In operation, if the cycle time of the computer 1 is sufficiently fast (i.e. about ¼ of the time between successive digitizations) than path A applies and digitized ion cyclotron resonant transient information (data set) is transferred directly from the analog-to-digital converter 5 to the computer 1 to be Fourier transformed as hereinafter described. Alternatively, if the cycle time of the computer is not sufficiently fast by the previous criteria, then it is necessary for the digitized data to follow path B. In this case, the digitized data is first entered into a intermediate storage register, such as the shift register memory 6, illustrated in FIG. 1. When a complete data array has been digitized and stored in the shift register memory 6, a suitable command from the computer 1 causes the data to be transferred from the shift register memory 6 to the computer 1 at a transfer rate limited by the cycle time of the computer 1. Since control logic and interfacing circuitry suitable for carrying out this sequence of operations is well known in the computer art, it will not be discussed here.

It is emphasized here that the sequence of events illustrated in FIG. 3 is to be taken as illustrative, rather than definitive. For example, if it is desired that time delay between ion formation and ion excitation and detection be long, it may be desirable to carry out the shift register memory-to-computer transfer (path B) while a "quench" pulse (hereinafter described), ion formation pulse, and even an ion excitation pulse are still in progress for the next cycle of the sequence. This would be done, for example, in order to minimize the total cycle time for the signal-averaging cycle herein described.

In order to improve the signal-to-noise aspects of the received information, it is generally desirable to accumulate a number of digitized ion cyclotron resonant transient data sets before the resultant data is further manipulated in the manner herein described. In other words, it is desirable to cycle the apparatus of the invention and obtain sequential sets of information. The word-by-word addition of the digitized ion cyclotron resonance transient data from one set to that of a previous set may be carried out continuously at the stage of transfer of digitized data from either the fast analog-todigital converter 5 or the shift register memory 6 to the computer 1, depending upon which mode of operation is being utilized. Since the ion cyclotron resonant transient information will increase in amplitude in accordance with the number of accumulated transients, while any random noise information will only increase in amplitude as the square-root of the number of accumulated transients, it is clear that the signal-to-noise ratio for any given ion cyclotron resonant transient response will increase as the square-root of the number of accumulated transients. Consequently, the number of transients to be accumulated for any particular set of conditions will be determined by the desired signal-to-noise ratio acceptable for the final ion cyclotron resonance spectrum.

As illustrated in FIG. 1, once the desired number of ion cyclotron resonant transient data sets has been accumulated in the computer 1, the resultant data may either be examined directly on an oscilloscope 8, plotted on either an analog X-Y recorder 9 or a digital X-Y recorder 11, printed out on a teletype 10, or transferred to a magnetic storage device 12 for later use. The magnetic storage device may consist of, but is not limited to, a magnetic cassette or reel-to-reel tape deck, or a magnetic disk system.

Alternatively, in accordance with this invention, the accumulated digitized ion cyclotron resonant transient data sets may be subjected to a discrete Fourier transformation to yield real and imaginary ion cyclotron resonance frequency spectra (each containing half as many data information points as did the original time-domain data set), either of which may be displayed. Following phase corrections described hereinafter, the ion cyclotron resonance frequency spectrum is displayed on the oscilloscope or the plotters, or stored in a magnetic storage device 12.

In order to obtain a uniform spectral display, wherein each of the ion cyclotron resonance spectral line shapes is of similar form, it is necessary to apply zero- and first-order phase corrections to the accumulated ion cyclotron resonant transient digitized data sets following Fourier transformation into a real and imaginary data array. Since such phase corrections are available as part of the usual software package accompanying any of several commercially available computers, such transformations are not discussed here. Alternatively, by taking the point-by-point sum of the squares of the real and imaginary data points resulting from the Fourier transformation of the accumulated original ion cyclotron resonant transient data sets, it is possible to obtain an "absolute-value" spectrum which exhibits a uniform spectral line shape even when there is a non-linear phase variation in the Fourier transformed accucmulated ion cyclotron resonant transient data sets. Again, since this procedure is well known to those skilled in the Fourier transformation art, it will not be described here.

Obviously, the absolute-value spectral display just described is not limited to use with frequency-sweep excitation. It may also be achieved with any suitable excitation, including either radio frequency pulse excitation or any of several types of pseudo-random ("stochastic") excitation hereinafter described.

It is pointed out here that one particular class of ion cyclotron resonance experiments is made relatively easy by the method and apparatus of the present invention. This class of experiments relates to the kinetics of ion-molecular reactions. In this experiment, a fixed time delay is initially specified for the interval between the completion of the ion formation pulse and the initiation of the ion excitation pulse illustrated in FIG. 3. Thereafter, a specified number of ion cyclotron resonance transient digitized data sets are accumulated in the manner previously described. When the desired number of data sets have been accumulated, the accumulation is transferred to the magnetic storage device 12. The whole procedure is then repeated for a different specified time delay until a desired number of accumulated data sets, corresponding to different time delays, have been stored in the magnetic storage device 12. Next, each of the stored accumulated data sets is individually subjected to Fourier transformation and phase correction as described above. Then, the corresponding ion cyclotron resonance frequency spectrum corresponding to each time delay is either plotted as a function of frequency (or mass-to-charge ratio) or stored in a separate region of the magnetic storage device 12, or both. The resultant information comprises a complete set of ion cyclotron resonance mass specra with each spectrum corresponding to a particular delay time between ion formation and ion excitation and detection. Using well known procedures of either a manual or computer nature allows the relative ion cyclotron resonance spectral intensity for each of the ion masses in the mass-to-charge range included in the experiment to be simultaneously determined as a function of delay time, and the various ion-molecular reaction rates determined from the rates of increase or decrease in the numbers of each ion of distinct mass-to-charge ratio. Obviously, the great advantage of the present invention over prior art ion cyclotron resonance spectroscopy methods and apparatus is its ability to observe a wide range of ionic mass-to-charge ratios in each experiment. Thus, the invention achieves great economy in observation period when compared to conventional prior art spectrometers which are limited to the observation of a single ion during the time interval equivalent to the time interval of the pulse sequence of the present invention.

Turning now to the final phase of the operational sequence illustrated in FIG. 3, subsequent to either mode A or mode B operation, a quench pulse is applied to one or more of the plates (illustrated as trapping plate 33) by its associated digital-to-analog converter 27 under the control of the computer 1. The quench pulse removes all ions from the interior of the ion resonance cell 3, after the ion cyclotron resonance detection portion of the cycle of operation is completed.

If positive (negative) ions are being examined using the apparatus of the invention, then the magnitude of the quench pulse is such that the trapping plate 33 is made more positive (negative) than any of the remaining plates. During the quench pulse period, all of the positive ions in the ion resonance cell 3 are driven toward the other trapping plate 36. If desired, the resultant ion current may be measured by the gated picoammeter 31. The computer 1 controls the timing of this measurement by applying a gating pulse to the gated picoammeter during the quench pulse period, so that current is measured only during that period. If it is desired to monitor the spurious loss of ions to plate 36 prior to the quench period, for example during the ion-molecule reaction time delay period, then the computer 1 applies a gating pulse to the picoammeter coincident with the delay period. Similarly, if it is desired to measure the total number of ions which are in the cell 3 at some intermediate time during the duty cycle illustrated in FIG. 3, then the quench pulse and a gating pulse (to the picoammeter) are applied at that period of time. Obviously, if the quench pulse is applied prior to the digitization period, then no ion cyclotron resonance signal will be detected. It will be appreciated that this aspect of the invention allows the number of ions present in the trapped ion cell 3 to be monitored at any particular period of time, as desired.

The foregoing has described a preferred embodiment of the invention; however, it will be obvious to those skilled in the art and others that various changes and modifications can be made therein without departing from the spirit and scope of the invention. For example, the timing sequence illustrated in FIG. 3 may be controlled by analog means, such as a voltage ramp sensed by comparator circuits, the comparator circuits in turn driving pulse circuits adapted to provide any or all of the illustrated pulses. Similarly, the voltages provided by the various digital-to-analog converters may be furnished by batteries and potentiometers, or operational amplifiers, or the like. In this regard, attention is directed to FIG. 5, which illustrates an apparatus for controlling the amplitude of necessary plate voltages using analog means while the timing sequence and duration of the various pulses used are controlled using digital means, under the control of the computer 1. This apparatus provides a particularly convenient method for controlling the individual voltages applied to the various plates forming the ion resonance cell 3.

Figure 5:
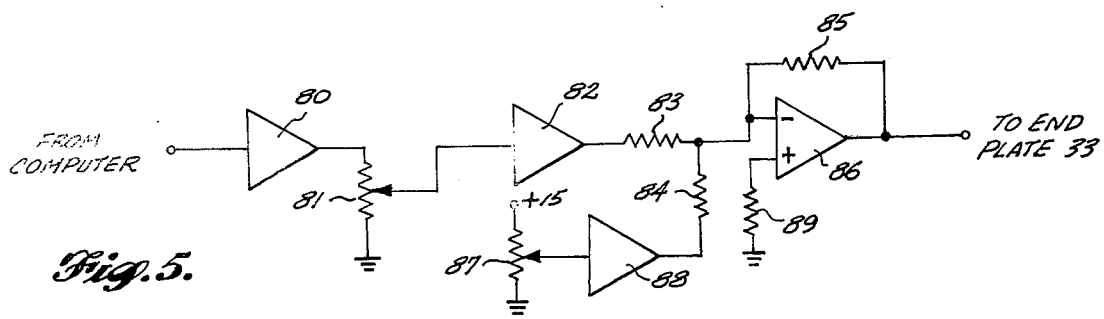
FIG. 5 is a schematic diagram of a circuit including an analog means for controlling the amplitude of voltages that is suitable for use in combination with a digital means for controlling the timing sequence and duration of various applied pulses.

FIG. 5 illustrates three buffer amplifiers 80, 82 and 88; an operational amplifier 86; two potentiometers 81 and 87; and, four resistors 83, 84, 85, and 89. It should be pointed out here that FIG. 5 is an exemplary circuit and, as illustrated, is adapted to control the voltage and amplitude applied to one of the plates, namely plate 33. Obviously, similar circuits will be needed to control the voltages applied to the other plates.

The computer 1 is connected to the first buffer amplifier 80, which provides isolation between the computer output and the further circuitry illustrated in FIG. 5. Thus, pulses generated by the computer to be applied to the circuit illustrated in FIG. 5 are received by the first buffer amplifier 80. The output of the first buffer amplifier 80 is connected across the first potentiometer 81. The movable element of the first potentiometer 81 is connected to the input of the second buffer amplifier 82. The output of the second buffer amplifier 81 is applied via the first resistor 83 to the inverting input of the operational amplifier 86.

The second potentiometer 87 is connected between a DC voltage source having a suitable voltage level, for example +15 volts, and ground. The movable element of the second potentiometer 87 is connected to the input of the third buffer amplifier 88. The output of the third buffer 88 is connected through the second resistor 84 to the inverting input of the operational amplifier 86. (It will be understood by those skilled in the analog computer art that the first and second resistors 83 and 84 are adding resistors.) The third resistor 85 is a feedback resistor connected between the output of the operational amplifier 86 and its inverting input. The non-inverting input of the operational amplifier 86 is connected through the fourth resistor to ground. The output of the operational amplifier is connected to the plate which it is intended to control, in this case end plate 33.

It will be appreciated by those skilled in the analog computer arts that the circuit comprising the operational amplifier 86, adding resistors 83 and 84, feedback resistor 85 and bias resistor 89 is a well known operational amplifier inverting adder circuit. Adjustment of the second potentiometer 87 establishes the quiescent voltage applied to the end plate 33. Adjustment of the first potentiometer 81 controls the height of the pulse applied to plate 33. The timing of the pulse is, of course, controlled by the computer 1.

It will be appreciated that it may be desirable in certain circumstances to use either a non-inverting circuit or a combination of inverting and non-inverting circuits to provide an add-subtract function, as opposed to the inverting circuit illustrated in FIG. 5. Such circuits are well known in the analog computer art. In this regard, attention is directed to "Application Manual for Operational Amplifiers," Philbrick/Nexus Research, Dedham, Mass., 02026 (1969) for a discussion of such amplifiers.

Preferably the gain of the first and second buffer amplifiers 80 and 82 is chosen to be either +1 or −1, depending upon the respective polarity of the desired pulse from the operational amplifier 86. In general, the pulse from the computer will have positive polarity and inversion of the output pulse may be necessary before that pulse is sent to the associated end plate 33, depending upon the circumstances of operation. Similarly, the polarity of the quiescent voltage on the end plate may be controlled by selection of the polarity of the DC voltage applied to the second potentiometer 87, or by choosing the gain of the third buffer amplifier 88 to be either +1 or −1. The polarity of both the quiescent voltage and the pulse polarity on the associated plate 33 may also be controlled by the wiring of the operational amplifier 86 so as to provide an add or subtract function, as is well known in the analog computer art.

As will be appreciated by those skilled in the ion cyclotron resonance art and others, the ion resonance cell 3 of the invention can take on a variety of forms. For example, rather than being formed of relatively solid trapping and side plates, any or all of the plates may be replaced by grids. Or, the trapping plates may be replaced by a plurality of plates connected to the DC voltage sources having different levels. Such a structure will improve the mass resolution of the invention. Moreover, the relative dimensions of the plates may differ from that illustrated in FIG. 2. A cell of modified dimensions will be particularly desirable when a solenoidal magnet is used to create the unidirectional magnetic field 18. Specifically, when such a solenoidal magnet is used, it will be desirable to increase the relative distance between the trapping plates as compared to the relative distance between the pairs of opposite side plates. Furthermore, as illustrated in FIG. 4 and hereinafter described, the side plates may be curved in order to improve the operation and sensitivity of the cell.

FIG. 4 illustrates an ion resonance cell 300 having a cylindrical shape. The cylindrical side walls are broken into four sections 320, 340, 350, and 370. The sections are equal in dimensions and are spaced from one another. Two of the sections, 320 and 350 form one set of side plates and the other two opposing sections 340 and 370 form the other side plates. (If desired, only two spaced semicylindrical side plates need be included, one forming essentially one side of the cylinder, and the other forming the other side.) The cylindrical structure is enclosed by a pair of trapping plates 330 and 360 which have suitable central apertures. The electron beam generated by a filament 150 and a grid 160 passes longitudinally through the central apertures in the trapping plates and the interior of the cylindrical ion resonance cell 300. The emitted electrons are collected by a collector plate 170. A solenoidal magnet formed by a coil 380 surrounds the exterior of the cylindrical ion resonance cell in a manner such that it creates a uniform magnetic field that extends between the trapping plates 330 and 360. (It will be appreciated by those skilled in the art that in an actual embodiment of the invention, the coil 380 will be physically located outside of the evacuation chamber, as well as outside of the cell 300). It will be noted at this point that the reference numbers used in FIG. 4 for the components of the cell 300 correspond to those used in FIG. 2 with the addition of a zero (0) suffix. Thus, the manner of connecting the cell illustrated in FIG. 4 to the previously described electronic system will be readily apparent.

Obviously, many modifications may be made to the connections running from the plates forming the ion resonance cell 3 to the other elements making up the overall ion resonance spectrometer illustrated in FIG. 2. For example, the junction between the two capacitors connected to the output of the amplitude control circuit may be made to any of the other side plates, 34, 37 or 32, rather than to the illustrated side plate 35. Furthermore, the connection to the broad-band amplifier 47 may be made to any of the other plates, 37, 34 or 35, rather than to the illustrated plate 32. In addition, it is not necessary that the connections from either capacitor 40 or 41, or the broad-band amplifier 47, be to only one plate of the ion resonance cell 3. For example, the radio frequency output of the capacitor 40 coupled to the amplitude control circuit 39 may be applied to a transformer, the secondary winding of which is connected to a pair of opposing plates, such as plates 32 and 35 to provide a push-pull alternating electric field in the cell. In this regard, attention is directed to FIG. 6 which illustrates a circuit suitable for making a connection in this manner.

Figure 6:
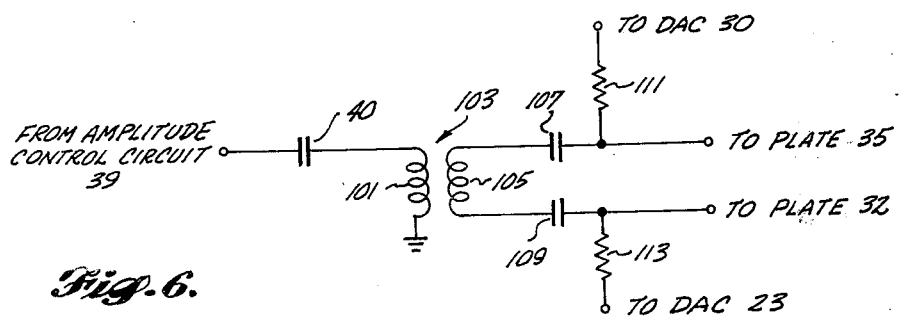
FIG. 6 is an alternate coupling circuit suitable for coupling a pulsed broad-band oscillating electric field signal to a trapped ion cell in push-pull manner.

In FIG. 6 the terminal of capacitor 40, opposite to the terminal connected to the amplitude control 39, is connected through the primary winding 101 of a transformer 103 to ground. The secondary winding 105 of the transformer 103 has its ends connected to opposed side plates 32 and 35 through suitable RF coupling capacitors 107 and 109. In addition, RF blocking resistors 111 and 113 are connected between these side plates and their associated digital-to-analog converters to provide RF blocking.

Figure 7:
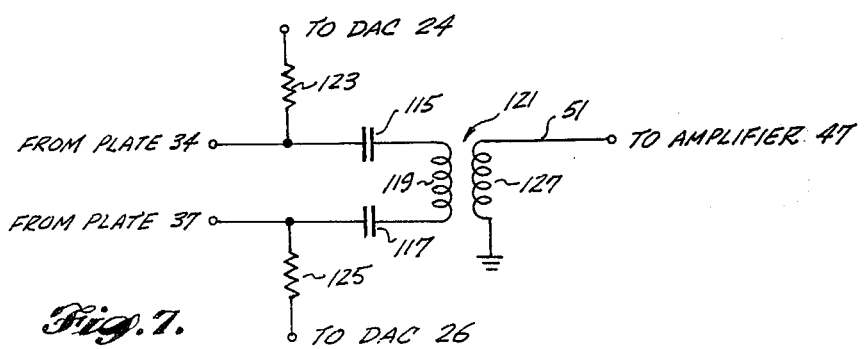
FIG. 7 is a schematic diagram illustrating an alternate circuit for transformer coupling a trapped ion cell to a broad-band amplifier.

In a substantially similar manner, the primary winding of a transformer may be connected to a pair of plates, such as side plates 34 and 37 and the secondary winding of the transformer may be connected to ground and to the input of the broad-band amplifier 47. A circuit for accomplishing this connection is illustrated in FIG. 7. FIG. 7 illustrates that the associated side plates 34 and 37 are connected through suitable RF coupling capacitors 115 and 117 to the opposite ends of the primary winding 119 of a transformer 121. RF blocking resistors 123 and 125 are connected between these side plates and their associated digital-to-analog converters 24 and 26. The secondary winding 127 of the transformer 121 has one end connected to ground and the other connected via lead 51 to the broad-band amplifier 47.

While the computer 1 provides the most generally useful means for generating the Fourier transform of the digitized ion cyclotron resonance transient data sets, it is not necessary to use a computer because analog Fourier analyzers are commercially available. These devices provide an inexpensive and reliable means for obtaining the Fourier transform spectra of any time-domain stored digitized data set in any desired phase mode, while correcting for zero- and first-order variations of phase with frequency. When the time-domain transient signal consists of the superimposition of one or more exponentially decaying sine waves, such Fourier analyzers provide a frequency resolution that is twice as good as a computer employing the well known Cooley-Tukey algorithm.

As briefly noted above, the broad-band, short-duration radio frequency excitation used to increase the radii of the cyclotron orbits of ions of a wide range mass-to-charge ratios should not be construed as limited to being generated by a frequency-sweep excitation device such as a remote programmable frequency synthesizer. For example, the psuedo-random (but precisely reproducible) binary sequences generated by shift registers can be used to modulate the amplitude of the (fixed) frequency of a radio frequency oscillator to generate a stochastic irradiation spectrum which is essentially flat for any specified frequency region either to higher or lower frequency levels with respect to the radio frequency oscillator frequency. Alternatively, the psuedo-random binary sequence may be used to modulate the amplitude of a DC signal, to generate a stochastic irradiation spectrum which is essentially flat for any specified frequency region from DC up to the desired irradiation cut-off frequency. Also the required psuedo-random binary sequence may be taken directly from the computer 1 without use of special shift register sequences. In fact, the pseudo-random binary sequence may be derived from any source of reproducible pseudo-random noise voltage. The computer is used to initiate the pseudo-random binary sequence and to trigger the high-speed analog-to-digital converter 5 at fixed time intervals later. In this fashion, a series of digitized ion cyclotron resonance transient data sets may be accumulated in a manner such that the phase at any point of the transient is preserved from one transient to the next.

In order to recover the ion cyclotron resonance frequency spectrum from an ion cyclotron resonance transient response to a pseudo-random frequency excitation the signal-averaged digitized transient is subject to a base line correction and Fourier transformation in the computer, as previously described. When an absolute-value ion cyclotron resonance spectral display is desired, the computer is instructed to construct a point-by-point sum of the squares of the cosine and sine Fourier transforms of the digitized time-domain ion cyclotron resonance signal. Alternatively, when an absorption-mode or dispersion-mode ion cyclotron resonance spectral display is desired, the digitized time-domain ion cyclotron resonance signal is cross-correlated with the pseudo-random excitation. This cross correlation is preferably performed in the following manner. First, the pseudo-random excitation is itself subjected to Fourier transformation. Then, the result is complex-multiplied with the Fourier transform of the digitized transient response, subjected to phase corrections as previously described, and then subjected to Fourier transformation to yield an ion cyclotron resonance frequency domain spectrum. These digitized data reduction procedures are well known and, hence, will not be further described here. In any event, the result of the above procedures is to produce a uniform-phase ion cyclotron resonance frequency spectra from the ion cyclotron resonance transient responses to a pseudo-random frequency excitation. The pseudo-random binary sequence may be used to provide amplitude, frequency, or phase modulation of a fixed radio frequency oscillator output, as is well known in the art.

It is emphasized that an ion cyclotron resonance absolute-value spectrum may be obtained by Fourier transformation of the digitized ion cyclotron resonance time-domain response to an excitation of arbitrary waveform (i.e., the procedure is not limited to the specific pulse-, frequency-, sweep- and stochastic-waveforms already described), followed by point-to-point sum of the squares of the cosine and sine Fourier transforms of the digitized time-domain ion cyclotron resonance signal. Finally, an absorption-mode or dispersion-mode spectrum may be extracted from the ion cyclotron resonance response to an excitation of arbitrary waveform by carrying out a cross-correlation of the digitized time-domain ion cyclotron resonance signal with the digitized excitation function in a manner analagous to that just described for the spectral excitation waveform.

One of the principal advantages of the present invention is its ability to produce an ion cyclotron resonance frequency spectrum having improved signal-to-noise ratio and/or resolution when compared to a spectrum generated in the same length of time for the same mass-to-charge ratio range by prior art ion cyclotron resonance spectrometers. In this regard, a preferred procedure for optimizing resolution is hereinafter described. It will be appreciated that the mass-to-charge ratio resolution in Fourier transform ion cyclotron resonance is limited by two factors: the time constant, $t$, for disappearance of the transient ion cyclotron resonance signal, whether by way of removal of ions from the ion resonance cell through contact with one of the plates or by chemical reaction with a suitable neutral molecule, or by collisions with neutral molecules in which momentum transfer occurs; and the duration of the detection period T. In the limit condition where $T>>t$, (limit (a)), the width of an ion cyclotron resonance "absorption"-mode signal is $(2/t)$ seconds$^{-1}$ or $(1/\pi t)$ Hz at half of the maximum amplitude in the frequency domain. For limit (a), then, it is necessary that the ions of two distinct mass-to-charge ratios differ in ion cyclotron resonance frequency by more than $(1/\pi t)$ Hz in order that the two absorption mode signals exhibit resolved maximum intensity. On the other hand, if $T<<t$, (limit (b)) then the width at half maximum intensity of an ion cyclotron resonance absorption-mode signal is given by $(3.8/T)$ seconds$^{-1}$ or $(0.6/T)$ Hz. Thus, for limit (b), it is necessary that ions of two distinct charge-to-mass ratios differ in ion cyclotron resonance frequency by more than $(1/T)$ Hz in order that the two absorption-mode signals exhibit resolved maximal intensity. The absorption-mode signal variation with frequency for detection periods, T, which are intermediate between limits (a) and (b) is well known and requires no further elaboration. Since the time constant, $t$, varies inversely with gas pressure, there will always be a pressure sufficiently low that limit (b) applies for a specified data acquisition period, T. Once limit (b) has been reached the resolution for ions of any charge-to-mass ratio is determined solely by the acquisition period, T, the size of the digital data set in which the transient is stored, N, and the digitizing rate employed during the acquisition of the transient ion cyclotron resonance data, F, according to the following equation:

$$F \cdot T = N \tag{2}$$

The data points in Fourier transform ion cyclotron resonance frequency spectra are spaced every $(1/T)$ Hz. Thus, for a magnetic field [see equation (1)] for which an ion of charge-to-mass ratio 15 has a resonance cyclotron frequency of 2.0 MHz, an acquisition time of 4 milliseconds produces an absorption-mode line width which is uniformly 151 Hz throughout the entire mass-to-ratio range with an approximate line width of 0.3 mass-to-charge units at mass-to-charge ratio 240.

N in equation (2) is determined by the size of the computer memory (and the shift register memory 6 if the mode B detection, illustrated in FIG. 1, is used). F is determined by the magnitude of the lowest mass-to-charge ion which is to be detected. And, T follows directly from equation (2) and the specified values of N and F. In practice, the size of the computer memory is generally set to the maximum possible number of words, so that the mass-to-charge resolution is ultimately determined by the ion of lowest mass-to-charge ratio [and therefore the largest ion cyclotron frequency determined by equation (1)], since $F = 2f$, where $f$ is the largest frequency to be digitized by the analog-to-digital converter 5. In order to make F as small as possible so that in turn T may be made as long as possible and the resolution $(1/T)$ as small as possible, it is desirable to mix the output of the broad-band amplifier 47 with the output of the frequency synthesizer 48, and then extract the difference frequency with the low pass filter 50, as discussed above. If the mixing frequency from the synthesizer 48 is chosen to lie slightly above the largest ion cyclotron frequency to be observed, then, the signal which is actually digitized by the fast analog-to-digital converter 5 will span a much smaller frequency range than would the unmixed output received via the conductor 51. The low pass filter is used to reduce the amplitude of all signals at frequencies higher than $f$ to prevent their well known "foldover" into the displayed Fourier transform frequency range.

Prior art ion cyclotron resonance spectroscopy methods and apparatus have been employed in a number of studies, including studies of the sequence, energy dependence, and rates of ion-molecule reactions for either positive or negative ions, photo-detachment and photodissociation studies, double resonance studies and the like. The Fourier transform ion cyclotron resonance method and apparatus of the present invention possesses the capability to perform all of the above experiments, plus several unique advantages hereinafter set forth.

Obviously, the principal advantage of the present invention over prior art ion cyclotron resonance spectroscopy methods and apparatus is the rapidity with which an ion cyclotron resonance frequency spectrum can be obtained for a specified mass-to-charge range, signal-to-noise ratio, and mass-to-charge resolution. More specifically, most prior art ion cyclotron resonance spectrometers require about 25 minutes to obtain a typical ion cyclotron resonance frequency spectrum for a mass range of 15–240 atomic mass units for singly charged ions and a mass-to-charge resolution of one atomic mass unit per charge. On the other hand, the present invention only requires about 15 seconds to produce a spectrum with the same mass range and mass-to-charge resolution, and equal or better signal-to-noise ratio, and, in addition, the present invention will yield a signal-to-noise ratio at mass-to-charge = 15 which is about 16 times greater than that of prior art magnetic field-sweep devices.

A unique advantage of the present invention is its ability to obtain a mass-to-charge resolution which is much higher than that obtainable by prior art devices of a similar nature. As described above, mass-to-charge resolution may be made arbitrarily high for a homogeneous magnetic field simply by making the acquisition time sufficiently long at low pressure. No prior art ion cyclotron resonance spectrometer has possessed this capability.

Further advantages of the present invention over prior art devices follow directly from its ability to operate at a fixed value of magnetic field strength. More specifically, such operation results in the production of ion cyclotron resonance frequency spectra which are equivalent to those which could be obtained by continuously monitoring the ion cyclotron resonance response to a continuous or discrete frequency sweep excitation. Thus, the present Fourier transform ion cyclotron resonance spectrometer can be continuously operated at a magnetic field strength which is equal to the maximum magnetic field strength reached in prior art magnetic field sweep spectrometers. More specifically, it is well known that ion cyclotron resonance sensitivity is proportional to magnetic field strength. Thus, when the spectrometer of the present invention is operated so as to achieve a sensitivity which is equal to the sensitivity of a conventional ion cyclotron resonance spectrometer for the largest mass-to-charge ion in a mass-to-charge spectrum, it automatically produces a higher sensitivity for all ions having a smaller mass-to-charge ratio. Because the magnetic field strength in prior art instruments varies, this advantage cannot be achieved by such instruments. A second advantage is that spurious effects due to space charge, which may vary inversely with magnetic field strength, are obviously minimized because the maximum magnetic field strength possible with the present invention is continuously being applied. Third, the use of a permanent magnet or fixed-field super conducting solenoidal magnet is possible with the present invention. Such magnets cannot be used in prior art magnetic field-sweep spectrometers.

A further advantage of the present invention is its capability for high resolution ion cyclotron double resonance experiments in which one or all reactant ions are irradiated prior to the simultaneous detection of all other ions of a specified mass-to-charge range in the sample. Thus, with the present invention, it is possible to discover all the product ions which are coupled to a given reactant ion in a single experiment. Prior art ion cyclotron resonance spectrometers do not possess this capability.

A still further advantage of the present invention not possessed by any prior art methods and apparatus of a similar nature derives from the temporal separation between the excitation and detection periods of the total experimental operational cycle shown in FIG. 3. It is well known that second-order ion cyclotron resonance frequency shifts due to the electric trapping field of the spectrometer vary with the radius of the ion orbit. In prior art devices, if spectrometer detection occurs while the ion orbit is increasing, a second-order deterioration of the observed mass-to-charge resolution results. On the other hand, ion cyclotron resonance detection by the present invention only occurs after all ions have been excited to substantially common orbital radii. Thus, second-order ion cyclotron resonance line-broadening is minimized by the present invention.

A yet further advantage of the present invention is its capability of generating an ion cyclotron resonance absolute-value frequency spectrum. Such a spectrum exhibits a better signal-to-noise ratio than the absorption-mode spectrum obtainable by prior art spectrometers.

While a preferred embodiment of the invention has been illustrated as described, it will be appreciated by those skilled in the art and others that various changes can be made therein without departing from the spirit and scope of the invention. Hence, the invention can be practiced otherwise than as specifically described herein.

The embodiments of the invention in which an exclusive property or privilege is claimed are defined as follows:

1. A Fourier transform ion cyclotron resonance mass spectrometer comprising:

an evacuable chamber suitable for receiving a gaseous sample to be mass analyzed;

evacuation means connected to said evacuable chamber for reducing the atmospheric pressure in said chamber to a predetermined level;

an ion cyclotron resonance cell, including a plurality of electrode plates, mounted in said evacuable chamber;

ion forming means for ionizing gases located in said ion cyclotron resonance cell;

magnetic field means for creating a unidirectional magnetic field, said magnetic field means mounted so that said unidirectional magnetic field passes through said ion cyclotron resonance cell in a predetermined direction;

voltage means connected to said plurality of plates of said ion cyclotron resonance cell, said voltage means generating voltages of a level and a polarity adequate to trap substantially all ions of a given charge sign formed by said ion forming means in said ion cyclotron resonance cell, said unidirectional magnetic field means causing said trapped ions to move orbitally at angular frequencies dependent on the mass-to-charge ratio of individual ions;

broad-band excitation means connected to said ion cyclotron resonance cell for producing a broad-band electric field at right angles to said unidirectional magnetic field, said broad-band electric field exciting all ions trapped within said ion cyclotron resonance cell that have a mass-to-charge ratio falling within a predetermined range;

broad-band detection means connected to said ion cyclotron resonance cell for simultaneously detecting the number of ions of each different mass-to-charge ratio excited by said broad-band excitation means and for generating a single time domain analog signal containing information related to the magnitude and nature of said numbers;

digitizing means connected to said broad-band detection means for digitizing said time domain analog signal related to the magnitude and nature of the number of ions of each different mass-to-charge ratio so as to produce a time domain digital signal related to the magnitude and nature of said numbers; and, Fourier transform means connected to said digitizing means for transforming said time domain digital signal into a frequency domain signal containing information about the numerical magnitude and frequency of excited ions of each different mass-to-charge ratio trapped in said ion cyclotron resonance cell.

2. A Fourier transform ion cyclotron resonance mass spectrometer as claimed in Claim 1 wherein:

said ion cyclotron resonance cell includes a plurality of plates mounted such that said plates enclose a predetermined volume, said plurality of plates including a pair of opposed trapping plates; and, said ion forming means generates an ionizing beam, said ion cyclotron resonance cell being mounted in a manner such that said ionizing beam passes therethrough.

3. A Fourier transform ion cyclotron resonance mass spectrometer as claimed in Claim 2 wherein said unidirectional magnetic field passes through said ion cyclotron resonance cell, in a direction orthogonal to said trapping plates.

4. A Fourier transform ion cyclotron resonance mass spectrometer as claimed in claim 3 wherein said voltage means applies a voltage to each of said plates, said voltages having levels and polarities adequate to create a static electric field within said ion cyclotron resonance cell adequate to trap within said cell substantially all ions of a given charge sign.

5. A Fourier transform ion cyclotron resonance mass spectrometer as claimed in claim 4 wherein said broadband excitation means creates a pulsed broad-band oscillating electric field.

6. A Fourier transform ion cyclotron resonance mass spectrometer as claimed in claim 5 wherein said broadband detection means comprises:

a broad-band amplifier connected to at least one of said plates of said ion cyclotron resonance cell for detecting excited ion cyclotron motion;

a signal generating means for producing a signal at a desired frequency;

a mixer having one input connected to the output of said signal generating means and a second input connected to the output of said amplifier for mixing said signals; and, a low pass filter connected to the output of said mixer for passing only the portion of the output of said mixer lying below a predetermined frequency.

7. A Fourier transform ion cyclotron resonance mass spectrometer as claimed in claim 5 including a frequency and amplitude controllable frequency generator that produces an oscillating electric field at a predetermined frequency related to the resonant frequency of ions of a predetermined mass-to-charge ratio prior to said pulsed broad-band oscillating electric field being produced.

8. A Fourier transform ion cyclotron resonance mass spectrometer as claimed in claim 5 wherein said pulsed broad-band oscillating electric field is produced by a frequency and amplitude controllable frequency generator.

9. A Fourier transform ion cyclotron resonance mass spectrometer as claimed in claim 8 wherein said frequency and amplitude controllable frequency generator that produces said pulsed broad-band oscillating electric field is a frequency synthesizer.

10. A Fourier transform ion cyclotron resonance mass spectrometer as claimed in claim 5 wherein said voltage means is adapted to apply a quench pulse to one of said plates.

11. A Fourier transform ion cyclotron resonance mass spectrometer as claimed in claim 10 wherein said quench pulse is applied to one of said trapping plates; and, including a gated picoammeter connected between the output of said voltage means connected to the other trapping plate, and the other trapping plate, so as to sense the ion current created when said quench pulse is applied to said one of said trapping plates.

12. A Fourier transform ion cyclotron resonance mass spectrometer as claimed in claim 10 wherein said ion forming means generates a pulsed electron beam.

13. A Fourier transform ion cyclotron resonance mass spectrometer as claimed in claim 1 wherein said voltage means applies a voltage to each of said plates, said voltages having levels and polarities adequate to create a static electric field within said ion cyclotron resonance cell adequate to trap within said cell substantially all ions of a given charge sign.

14. A Fourier transform ion cyclotron resonance mass spectrometer as claimed in claim 13 wherein said voltage means is adapted to apply a quench pulse to one of said plates.

15. A Fourier transform ion cyclotron resonance mass spectrometer as claimed in claim 14 including an accumulation means connected to said digitizing means for accumulating a plurality of said time domain digital signals related to the numerical magnitude of ions of different mass-to-charge ratios prior to said Fourier transform means transforming said time domain digital signals into a frequency domain signal containing information about the numerical magnitude and frequency of ions of each different mass-to-charge ratio trapped in said ion cyclotron resonance cell.

16. A Fourier transform ion cyclotron resonance mass spectrometer as claimed in claim 1 wherein said broad-band detection means comprises:

a broad-band amplifier connected to at least one of said plates of said ion cyclotron resonance cell for detecting ion cyclotron motion;

a signal generating means for producing a signal at a desired frequency;

a mixer having one input connected to the output of said signal generating means and a second input connected to the output of said amplifier for mixing said signals; and, a low pass filter connected to the output of said mixer for passing only the portion of the output of said mixer lying below a predetermined frequency.

17. A Fourier transform ion cyclotron resonance mass spectrometer as claimed in claim 1 wherein said broad-band detection means comprises:

a broad-band amplifier connected to at least one of said plates of said ion cyclotron resonance cell for detecting ion cyclotron motion; and, a low pass filter connected to the output of said amplifier for passing only the portion of the output of said amplifier lying below a predetermined frequency.

18. A Fourier transform ion cyclotron resonance mass spectrometer as claimed in claim 1 wherein said ion forming means generates a pulse electron beam.

19. A Fourier transform ion cyclotron resonance mass spectrometer as claimed in claim 1 wherein said broad-band excitation means creates a pulsed broad-band oscillating electric field.

20. A Fourier transform ion cyclotron resonance mass spectrometer as claimed in claim 19 wherein said broad-band oscillating electric field is produced by a frequency and amplitude controllable frequency generator.

21. A Fourier transform ion cyclotron resonance mass spectrometer as claimed in claim 20 wherein said frequency and amplitude controllable frequency generator is a frequency synthesizer.

22. A Fourier transform ion cyclotron resonance mass spectrometer as claimed in claim 20 wherein said frequency and amplitude controllable frequency generator produces a pseudo-random noise signal.

23. An ion cyclotron resonance mass spectrometer as claimed in claim 1 including a frequency and amplitude controllable frequency generator that produces an oscillating electric field at a predetermined frequency related to the resonant frequency of ions of a predetermined mass-to-charge ratio prior to said pulsed broad-band oscillating electric field being produced.

24. A Fourier transform ion cyclotron resonance mass spectrometer as claimed in claim 1 wherein said plurality of plates comprises first and second trapping plates and a plurality of curved plates disposed so as to define a segmented cylinder.

25. In an ion cyclotron resonance mass spectrometer wherein an ion cyclotron resonance cell formed of a plurality of plates is mounted in an evacuable chamber suitable for receiving a gaseous sample to be ionized by an ion-forming means, said ions being trapped in orbits within said ion cyclotron resonance cell by unidirectional magnetic field in combination with a static electric field, the improvement comprising:
  broad-band excitation means suitable for applying a broad-band electric field at right angles to said unidirectional magnetic field to said ions trapped in said ion cyclotron resonance cell so as to accelerate all trapped ions that lie within a predetermined mass-to-charge ratio range to larger radius orbits; and,
  broad-band detection means suitable for detecting said accelerated ions and producing a time domain signal containing information related to the number of ions of specific mass-to-charge ratios which are accelerated by said broad-band electric field.

26. An improved ion cyclotron resonance mass spectrometer as claimed in claim 25 wherein said broad-band electric field is a pulsed broad-band oscillating electric field.

27. An improved ion cyclotron resonance mass spectrometer as claimed in claim 26 wherein said pulsed broad-band oscillating electric field is produced by a frequency and amplitude controllable frequency generator.

28. An improved ion cyclotron resonance mass spectrometer as claimed in claim 27 wherein said frequency and amplitude controllable frequency generator is a frequency synthesizer.

29. An improved ion cyclotron resonance mass spectrometer as claimed in claim 25 including a frequency and amplitude controllable frequency generator that produces an oscillating electric field at a predetermined frequency related to the resonant frequency of ions of a predetermined mass-to-charge ratio prior to said broad-band electric field being produced.

30. An improved ion cyclotron resonance mass spectrometer as claimed in claim 25 wherein said broad-band detection means comprises:
  a broad-band amplifier connected to at least one of said plates of said ion cyclotron resonance cell for detecting excited ion cyclotron motion;
  a signal generating means for producing a signal at a desired frequency;
  a mixer having one input connected to the output of said signal generating means and a second input connected to the output of said amplifier for mixing said signals; and,
  a low pass filter connected to the output of said mixer for passing only the portion of the output of said mixer lying below a predetermined frequency.

31. An improved ion cyclotron resonance mass spectrometer as claimed in claim 25 wherein said broad-band detection means comprises:
  a broad-band amplifier connected to at least one of said plates of said ion cyclotron resonance cell for detecting ion cyclotron motion; and,
  a low pass filter connected to the output of said broad-band amplifier for passing only the portion of the output of said broad-band amplifier lying below a predetermined frequency.

32. A method of Fourier transform ion cyclotron resonance spectroscopy comprising the steps of:
  ionizing a gas sample located within an analyzer cell mounted in an evacuable chamber during an ionizing period;
  trapping substantially all ions of a given charge sign formed within the analyzer cell during and after the ionization period and causing them to move obitally at an angular frequency by subjecting them to the combined action of static electric fields and a unidirectional magnetic field;
  exciting, during a broad-band ion cyclotron resonance excitation period, all ions trapped within the cell that lie within a range of mass-to-charge ratios by applying a broad-band exciting electric field to said analyzer cell in a direction substantially transverse to the direction of said unidirectional magnetic field;
  converting said excited ion cyclotron motion of ions falling within said range of mass-to-charge ratios into a time domain analog signal;
  digitizing said analog signal in the time domain to form a time domain digital signal; and,
  converting said time domain digital signal into a frequency domain signal.

33. A method of Fourier transform ion cyclotron resonance spectroscopy as claimed in claim 32 including the step of reducing the frequency range of said time domain analog signal prior to digitizing said time domain analog signal.

34. A method of Fourier transform ion cyclotron resonance spectroscopy as claimed in claim 32 including the step of quenching substantially all of said trapped ions during a quench period occurring subsequent to said ionizing, trapping, exciting, converting, and digitizing sequence.

35. A method of Fourier transform ion cyclotron resonance spectroscopy as claimed in claim 34 including the steps of:
sequentially repeating the steps of ionizing, trapping, exciting, converting, digitizing and quenching to create a plurality of time domain digital signals; and,
accumulating said plurality of time domain digital signals, prior to converting said time domain digital signals to a frequency domain signal.

36. A method of Fourier transform ion cyclotron resonance spectroscopy as claimed in claim 35 including a reaction time delay period between said step of trapping substantially all ions of a given charge formed within said analyzer cell and said step of exciting said trapped ions during said broad-band ion cyclotron resonance excitation period of each of said sequences.

37. A method of Fourier transform ion cyclotron resonance spectroscopy as claimed in claim 36 including the step of varying the reaction time delay period during succeeding ionizing, trapping, exciting, converting, digitizing and quenching sequences in order to determine the concentration of ions of different distinct mass-to-charge ratios lying within said range of mass-to-charge ratios, as a function of said reaction time.

38. A method of Fourier transform ion cyclotron resonance spectroscopy as claimed in claim 36 including the step of exciting a group of trapped ions at their resonant frequency by subjecting them to an irradiating pulse created by a pulsed oscillating electric field applied transversely to said unidirectional magnetic field during a double irradiating period occurring prior to said broad-band ion cyclotron resonance excitation period to impart energy to said group of trapped ions, in order to determine simultaneously the concentrations of many ions of different distinct mass-to-charge ratios lying within said range of mass-to-charge ratios as a function of the intensity of said irradiating pulse.

39. A method of Fourier transform ion cyclotron resonance spectroscopy as claimed in claim 38 including the step of varying the reaction time delay period during succeeding ionizing, trapping, exciting, converting, digitizing and quenching sequences in order to determine the concentration of ions of different distinct mass-to-charge ratios lying within said range of mass-to-charge ratios, as a function of said reaction time.

40. A method of Fourier transform ion cyclotron resonance spectroscopy as claimed in claimed 32 wherein said broad-band ion cyclotron resonance excitation is achieved by varying the frequency of the output of a source of alternating voltage during said ion cyclotron resonance excitation period.

41. A method of Fourier transform ion cyclotron resonance spectroscopy as claimed in claim 32 wherein said broad-band ion cyclotron resonance excitation is achieved by modulating an alternating carrier voltage by intermittent phase modulation provided by a repeatable pseudo-random noise sequence.

42. A method of Fourier transform ion cyclotron resonance spectroscopy as claimed in claim 32 including the step of irradiating said trapped ions with photons prior to said excitation period.

43. A method of Fourier transform ion cyclotron resonance spectroscopy as claimed in claim 32 including the steps of:
sequentially repeating the steps of ionizing, trapping, exciting, converting and digitizing to create a plurality of time domain digital signals; and,
accumulating said plurality of time domain digital signals, prior to converting said time domain digital signals to a frequency domain signal.

* * * * *